United States Patent [19]

Cox et al.

[11] Patent Number: 4,999,102
[45] Date of Patent: Mar. 12, 1991

[54] LIQUID TRANSFER MANIFOLD SYSTEM FOR MAINTAINING PLUG FLOW

[75] Inventors: John R. Cox, Twin Falls; Edward G. Bulgin, Nampa, both of Id.

[73] Assignee: The Amalgamated Sugar Company, Ogden, Utah

[21] Appl. No.: 285,732

[22] Filed: Dec. 16, 1988

[51] Int. Cl.⁵ .............................................. F16L 41/00
[52] U.S. Cl. ................... 210/137; 137/561 A; 138/44; 210/284; 210/456; 422/220
[58] Field of Search ............ 210/96.1, 97, 101, 198.2, 210/264, 279, 289, 291, 292, 293, 456, 656, 659, 266, 284, 278, 137; 55/67, 171, 197, 386; 127/46.2; 137/561 A; 422/220; 138/44

[56] References Cited

U.S. PATENT DOCUMENTS

| | | | |
|---|---|---|---|
| 2,985,589 | 5/1961 | Broughton et al. | 210/264 |
| 3,208,833 | 9/1965 | Carson | 210/284 |
| 3,214,247 | 10/1965 | Broughton | 210/284 |
| 3,523,762 | 8/1970 | Broughton | 210/284 |
| 4,161,963 | 7/1979 | Stevens | 210/289 |
| 4,208,284 | 6/1980 | Pretorius et al. | 55/386 |
| 4,354,932 | 10/1982 | McNeil | 210/291 |
| 4,378,292 | 3/1983 | Haase | 210/266 |
| 4,409,033 | 10/1983 | LeRoy | 210/278 |
| 4,412,866 | 11/1983 | Schoenrock et al. | 210/656 |
| 4,478,721 | 10/1984 | Gerhold | 210/659 |
| 4,565,216 | 1/1986 | Meier | 137/561 A |
| 4,609,009 | 9/1986 | Tisone | 137/561 A |
| 4,673,507 | 6/1987 | Brown | 210/289 |

Primary Examiner—Robert A. Dawson
Assistant Examiner—Joseph Drodge
Attorney, Agent, or Firm—Trask, Britt & Rossa

[57] ABSTRACT

A manifold system is constructed for evenly distributing a liquid to, and/or evenly collecting a liquid from, a cell of a separator system. The flow paths between the manifold inlet(s) and manifold outlet(s) are all approximately hydraulically identical in numbers, types, and dimensions of flow components, such that: (a) the flow rates to/from each of multiple inlets/outlets is equivalent, even with changes in overall pressure drop or flow rate, and (b) the time required for liquid to traverse each of the manifold flow paths is approximately identical, enabling plug flow through the cell.

6 Claims, 4 Drawing Sheets

LIQUID TRANSFER MANIFOLD SYSTEM FOR MAINTAINING PLUG FLOW

BACKGROUND

1. Field

This invention relates to industrial scale uniform distribution and collection devices. It is particularly directed to liquid transfer manifold systems for use in columns or cells constituting a portion of a separator system, such as those involving chromatographic separation, ion exclusion, or ion exchange, specifically including simulated moving beds and adsorber-desorber systems.

2. State of the Art

Performance design criteria have evolved in connection with large-scale separators (those with columns or cells having diameters of two feet and larger) as follows:

(1) There must be uniform distribution of the liquid phase across the surface of the solid phase media.

(2) The collection system must be conducive to plug flow of the liquid phase through the solid phase media.

(3) The composition of fluid flowing through most separation systems alternates between two or more liquid phases. Usually, the feed stock and the eluate phases are present, and often an extract, raffinate or other phases are also present. The distribution ad collection systems should maintain a well-defined interface between the various liquid phases flowing through the system. Once a separation of components occurs, the resulting discrete phases should be kept separate by maintaining plug flow characteristics. "Plug flow" implies that respective liquid interfaces of a phase plug reach, respectively, and approximately simultaneously, the distributor closest to an inlet and an outlet remote from that inlet. The same principle applies to the collection system.

(4) To maintain phase separation between liquid phases, it is desirable to minimize the void between a distributor (or collector) and the surface of the solid phase, thereby reducing the opportunity for backmixing. Any orifice or nozzle system functioning as a distributor and/or a collector should be in contact with, or at least in near proximity to, the surface of the solid phase media at all times. Structure associated with these elements should desirably provide a barrier against which the solid media can be packed.

Various separator systems of the type contemplated by this invention are disclosed by U.S Pat. Nos. 2,985,599; 4,001,133; 4,182,633 and 4,412,866, the disclosures of which are incorporated by reference for their teachings concerning the operation and control of separator systems generally and for their illustration of various structures and mechanisms relied upon in the separation art for distributing liquids to an interface or collecting liquids from an interface. U.S. Pat. No. 4,412,866 is generally instructive, and FIG. 2 of that patent discloses representative distributor and collector devices improved upon by this invention.

As used herein and in the appended claims: The term "separator system" is intended to designate the apparatus of any unit operation, including those specifically identified by this disclosure, in which liquid is either introduced to or withdrawn from a cell at a zone approximately transverse the direction of flow through a cell. The term "cell" is intended to include the terms "vessel" and "column," as well as any other structure utilized by practitioners of the separation arts, to effect a separation and/or extraction of components from an admixture by bringing the admixture into contact with solid or liquid exchange media. "Cross-sectional zone" (or region) refers to a region within a cell bounded by cross sections of the cell oriented transverse (typically approximately normal) the longitudinal direction of flow through the cell. "Longitudinal direction of flow" refers to the direction of fluid flow from an inlet towards an outlet within a cell. "Longitudinal" is used consistently to designate the dominant flow path of fluid through a cell without regard to direction. "Hydraulically identical," as applied to conduits, plenums and the like, means that the elements compared react to pressure differentials in a fluid circuit as though they were structurally identical. "Distributor" (or "distribution system") refers to structure through which fluids are introduced to a cell and "collector"or ("collection system") refers to structure used to withdraw fluids from a cell, in each instance from a cross-sectional zone. The term "plenum" is defined in this application as a fluid flow device which receives fluid from a single inlet conduit and discharges the fluid into a plurality of outlet conduits, or receives fluid from a plurality of inlet conduits and discharges it into a single outlet conduit.

SUMMARY OF THE INVENTION

The present invention provides a manifold (header) system which can function as a distributor or a collector in a separation system. In either application, the manifold system maintains an interface between phases within a large scale cell; that is, a typical cell within a large-scale separator system. The manifold is of low internal volume, as compared to commonly used systems, thereby offering a reduced retention time.

In practice, the manifold of this invention may be used to introduce liquid(e.g. feed or eluent) to a cell at an inlet zone which occupies or constitutes a cross-sectional region of the cell. Introduction is through a multiplicity of fluid passage devices, typically nozzles. Liquid is delivered to the nozzles through the manifold by means of approximately hydraulically identical flow paths comprised of distribution plenums, tubing, and ancillary fixtures from a common feed plenum (center well). The nozzles are mounted or suspended within the inlet zone to deliver fluid at an approximately horizontal interface of a "plug" of discrete liquid composition. The multiplicity of fluid passage devices is arranged in a pattern which assures approximately even distribution of liquid across the entire cell at the interface. A theoretically ideal such pattern places each device (e.g., nozzle or orifice) to supply liquid to an approximately equal area of interface, with appropriate adjustments to take into account the effect of the walls and other internal structure contacted by the feed and/or the liquid plug. In practice, a substantial departure from a theoretical pattern is tolerable, provided the population of fluid passage devices is sufficiently large, taking into account the flow rate of liquid introduced through the manifold.

The fluid delivery components of the manifold, in addition to the liquid passage devices, comprise a center well, which is usually, but not necessarily, positioned at the center of the cell. This disclosure assumes, for the sake of simplicity of description, that the cell has a circular horizontal cross section and is oriented approximately vertically; e.g., as an upstanding column. It is recognized that cells can be fashioned with other cross-sectional configurations, and that in some circumstances plug flow or circulation may be established with substantial horizontal components. Nevertheless, this disclosure, being directed to the preferred embodiments, will emphasize the typical cell configuration, with the understanding that the invention can be appropriately modified for incorporation in other configurations.

In any event, the center well is hydraulically symmetrical, typically being fashioned as an open cylinder fed by fluid delivery means, such as a launder, pipe, injector or drain. In most instances, feed to the well is at the top, through an adjustable flow regulator. In a typical arrangement, hydraulically equivalent piping runs (conduits, elbows, orifices, valves, flow regulators and/or similar components) extend from the well at approximately equally spaced radial locations around the circumference of the well. This arrangement constitutes the simplest, and thus generally preferred, case. Those skilled in the art are well able to devise various hydraulically equivalent arrangements. Each piping run (which may constitute a single straight conduit, which may be called a primary—or primary distribution—conduit) is in open fluid flow communication with the well at a proximal end, and terminates in open fluid flow communication with an intermediate plenum.

The intermediate plenums, which correspond in number to the number of primary conduits (or like piping runs), may be structured similarly to the center well, and serve a similar liquid distribution function; namely, to transfer fluid at substantially the same hydraulic characteristics to remote locations.

The manifold system of this invention usually includes a convenient number of intermediate stages, with each succeeding stage including a step-down plenum receiving liquid through the terminal end of a conduit in open communication with a larger plenum closer (upstream in the case of a distributor) in the manifold circuit to the center well. In certain instances, intermediate stages may be dispensed with, but when they are present, each step-down stage includes plenums totaling in number the number of conduits extending in open fluid flow communication from the plenums of the next larger (stepped-up) stage. A final, or terminal, stage includes conduits of small cross section from any of the intermediate stages, and terminates in the aforementioned fluid passage devices.

Manifold systems similar, or even identical, in structural detail to the distributor systems described may be utilized as collection systems. The fluid passage devices of choice for a collection system may differ from those preferred for distribution systems, but simple orifices will suffice in many instances for both applications.

BRIEF DESCRIPTION OF THE DRAWINGS

In the drawings, which illustrate what is presently regarded as the best mode for carrying out the invention.

DESCRIPTION OF THE ILLUSTRATED EMBODIMENTS

Figure 1:
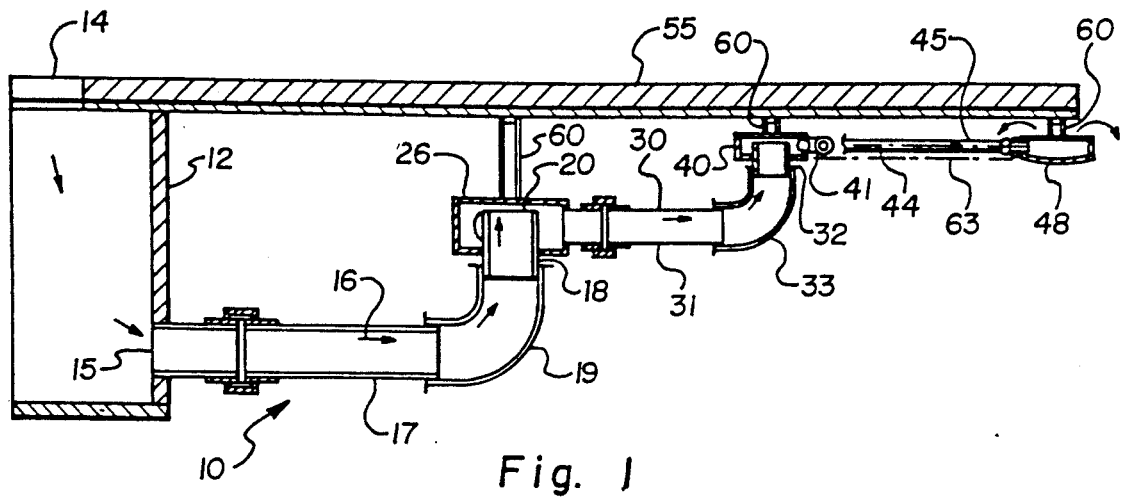
FIG. 1 is a view in section of a portion of a manifold system of the invention installed as a distributor.
Figure 2:
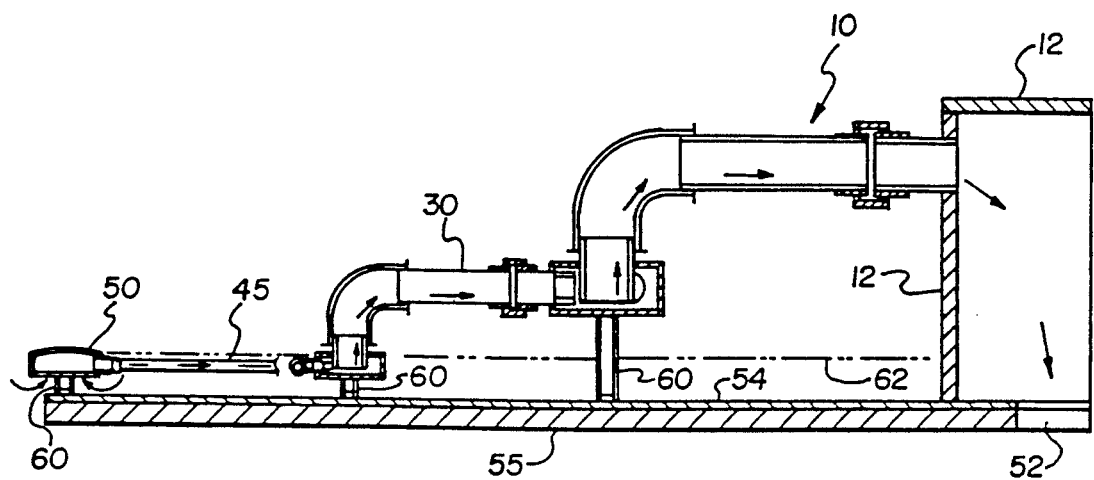
FIG. 2 is a view in section of apparatus similar to that of FIG. 1 installed as a collector.
Figure 3:
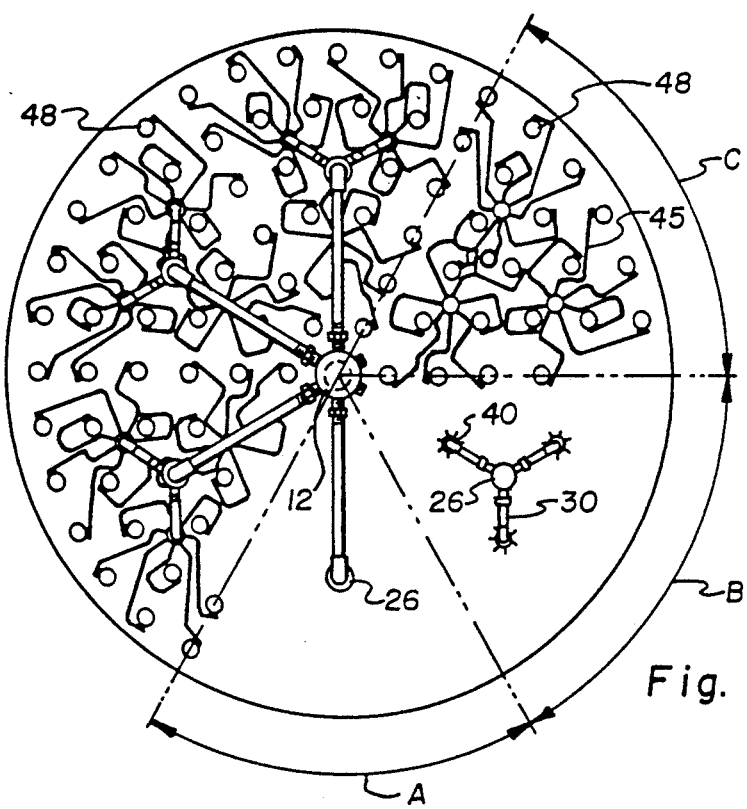
FIG. 3 is a fragmentary plan view illustrating a typical layout of a manifold system of this invention including three step-down stages.

FIGS. 1 and 2 illustrate substantially similar structure constituting a single leg, designated generally 10, of a manifold system of the type illustrated more completely by FIG. 3. As shown by FIG. 1, a center well 12, which is a cylindrical plenum, receives liquid through a port 14. The liquid then flows as indicated by the arrows into the proximal end 15 of the primary conduit, designated generally 16 and including pipe lengths 17 and 18 and elbow 19, to discharge through the terminal end 20 into an intermediate plenum 26. The system includes a plurality of primary conduits 16 extending at radially and equally spaced locations from the sidewall of the center well 12. In like fashion, a plurality of secondary conduits, indicated generally 30, and including pipe lengths 31 and 32 and elbow 33, provides fluid flow communication between the intermediate plenum 26 and a plurality of subsequent (as illustrated, terminal) plenums 40. The plurality of terminal plenums 40 corresponds in number to the plurality of secondary conduits 30 in the manifold system. Ideally, the respective flow paths from the center well to the individual outlets 41 of each terminal plenum 40 in the system are hydraulically equivalent so that the flow rate of liquid into the proximal ends 44 of tubing runs 45 is approximately identical. Each of the plurality of runs 45 terminates in open fluid flow communication with a fluid passage device, shown as a nozzle 48. The nozzles 48 are positioned in a pattern best shown by FIG. 3 with the individual tubing runs 45 taking whatever shape is required to accommodate the pattern. Practicalities of fabrication may make it impractical for the runs 45 to be hydraulically identical, but it is highly preferred for the discharges from the nozzles 48 to be nearly identical; i.e., within about three percent of the average of all nozzles, expressed as a flow rate (e.g., gallons per minute).

FIG. 2 illustrates a manifold segment substantially the same as that illustrated by FIG. 1, but installed as a portion of a collector. That is, the nozzles 50 are disposed in the vicinity of an outlet 52 and occupy an outlet zone 54 adjacent a structural plate 55. In both the distributor and collector arrangements illustrated by FIGS. 1 and 2, respectively, the manifold components are shown secured by structural elements 60 to a structural plate 55. The solid phase media will typically fill the entire volume of a cell, commencing with a lower interface 62 at the top of the zone 54 (typically filled with inert material such as sand or gravel) to an upper interface 63, which typically constitutes an interface between resin and air, water, oil or other fluid regarded as inert to the system.

It will be understood that the number of intermediate plenums, terminal plenums, and nozzles, as well as the placement patterns of the nozzles, will be determined in substantial part by the diameter of the cell and the nozzle density selected. The placement and arrangement of FIG. 3 is presently regarded as appropriate for a cell approximately 13 to 16 feet in diameter, in which fluid is delivered to an interface at approximately 200 to 700 gallons per minute. The illustrated placement pattern effects a flow rate of approximately 1 ½ to 5 ½ gallons per minute through each nozzle, and the number of nozzles is selected to provide a nozzle density of one nozzle for approximately each 1 to 1 ½ square feet of interface surface area. Other placement patterns may be preferred for large cells (e.g. up to 50 feet in diameter) or small cells (e g. as little as 2 feet in diameter).

FIG. 3 illustrates a center well 12 supplying six primary conduits 10 which deliver liquid to six intermediate plenums 26 (one of which is shown in segment A of the drawing). Each intermediate plenum 26 supplies three terminal plenums 40 through respective secondary conduits 30 (see segment B, FIG. 3). Each of the secondary plenums 40 delivers liquid through piping runs 45 to individual nozzles 48 (see segment C, FIG. 3). Although the drawings illustrate most of the manifold system attached to the interior sides of the structural plates 55, it is within contemplation that all, or substantial portions, of the conduits be external the cell. Only the nozzles need be internal the cell in practice.

Generally, the distributor and collector of this invention can be arranged to provide nearly identical hydraulic paths from an inlet well or outlet well 12 to each nozzle associated with that well. Good fluid distribution and hydraulic balance over a wide range of flow rates, e g. a maximum flow rate as much as 5 times the minimum flow rate in a system may be provided without the need for developing high pressure drops to force such distribution. In the preferred configurations, an identical distance is traversed between a well and each nozzle. In some cases, when this objective is impractical, known devices can be used to equalize the flow through various nozzles. It is within contemplation that such devices be adjustable and responsive to sensors within the cell to maintain nearly identical plug flow.

An important aspect of the invention is the ability to maintain hydraulic balance and even flow distribution without sacrificing plug flow. While the invention is especially advantageous to large diameter cells, it can be applied to cells of any size.

The following specific example is illustrative of the operation of this invention.

EXAMPLE

Figure 4:
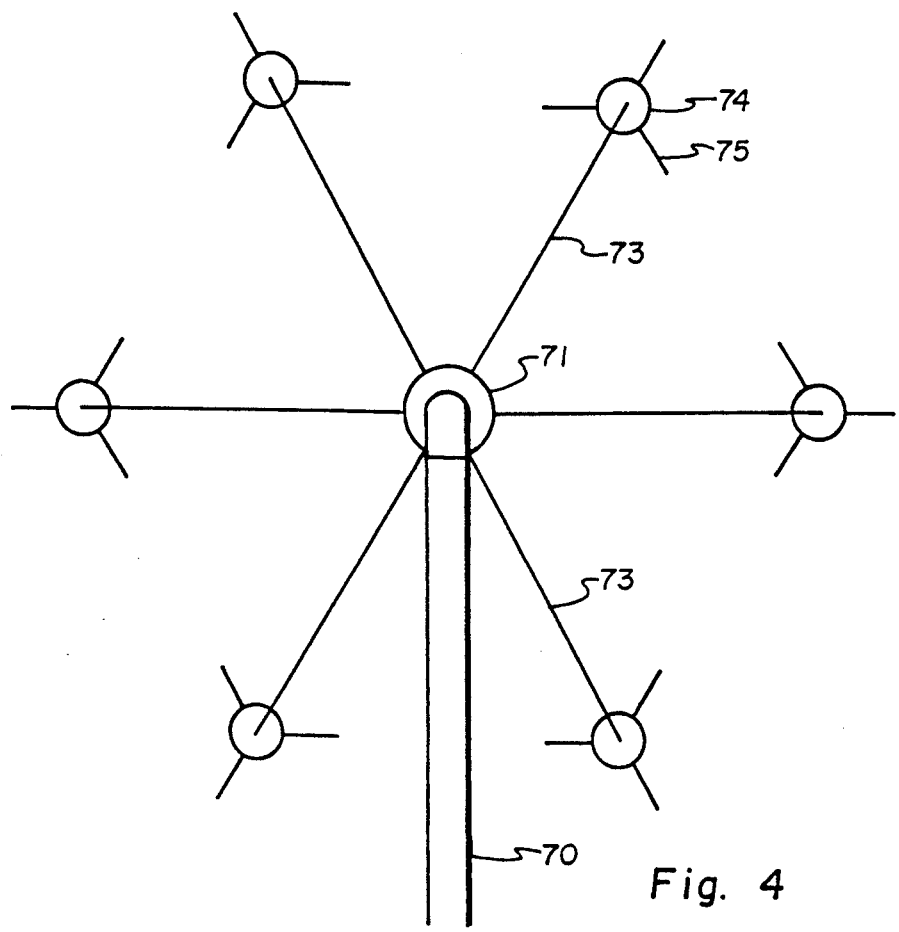
FIG. 4 is a schematic plan view of a single leg of a manifold of the type illustrated by FIG. 3.

FIG. 4 illustrates a structure which was assembled from PVC parts to simulate a segment of a manifold of the invention. A 2-inch diameter primary conduit, 70, which is regarded as one of several hydraulically equivalent such conduits fed by a hydraulically symmetrical center well feeds an intermediate plenum 71 structured as a cylinder 4 inches in diameter and 5 inches high. Six equal-length ¾-inch diameter secondary conduits 73 extend from equally radially spaced outlets in the sidewall of the plenum 71 to deliver liquid to the tops of six terminal plenums 74 constructed as cylinders 2 inches in diameter and 3 inches high. Three equally spaced ½-inch diameter conduits 75 of equal length extend radially from the sidewalls of each of the terminal plenums 74. The terminal ends of the smaller conduits 75 are regarded as equivalent to open orifice nozzles.

Water was introduced to the primary conduit 70 at a rate which produced flow rates in the smaller conduits 75 of between 2 and 4 gallons per minute. One of the secondary conduits was broken during the experiment, adversely affecting the results Nevertheless, flow rates were measured, and standard deviations in flow (excluding the flows associated with the broken secondary conduit) were calculated. The standard deviations of flows through the conduits 73 fed by the damaged (non-symmetrical) secondary plenum 71 ranged between 3.8 percent at low flow and 4.2 percent at high flow. The standard deviations of flow through the conduits 75 fed by the terminal plenums 74 (excluding that fed by the broken secondary conduit) averaged about 3 percent at low flow and about 2 percent at high flow. These results were considered to compare favorably with current industry standards, which typically tolerate a five percent deviation in flow rate across a large diameter vessel.

Figure 5:
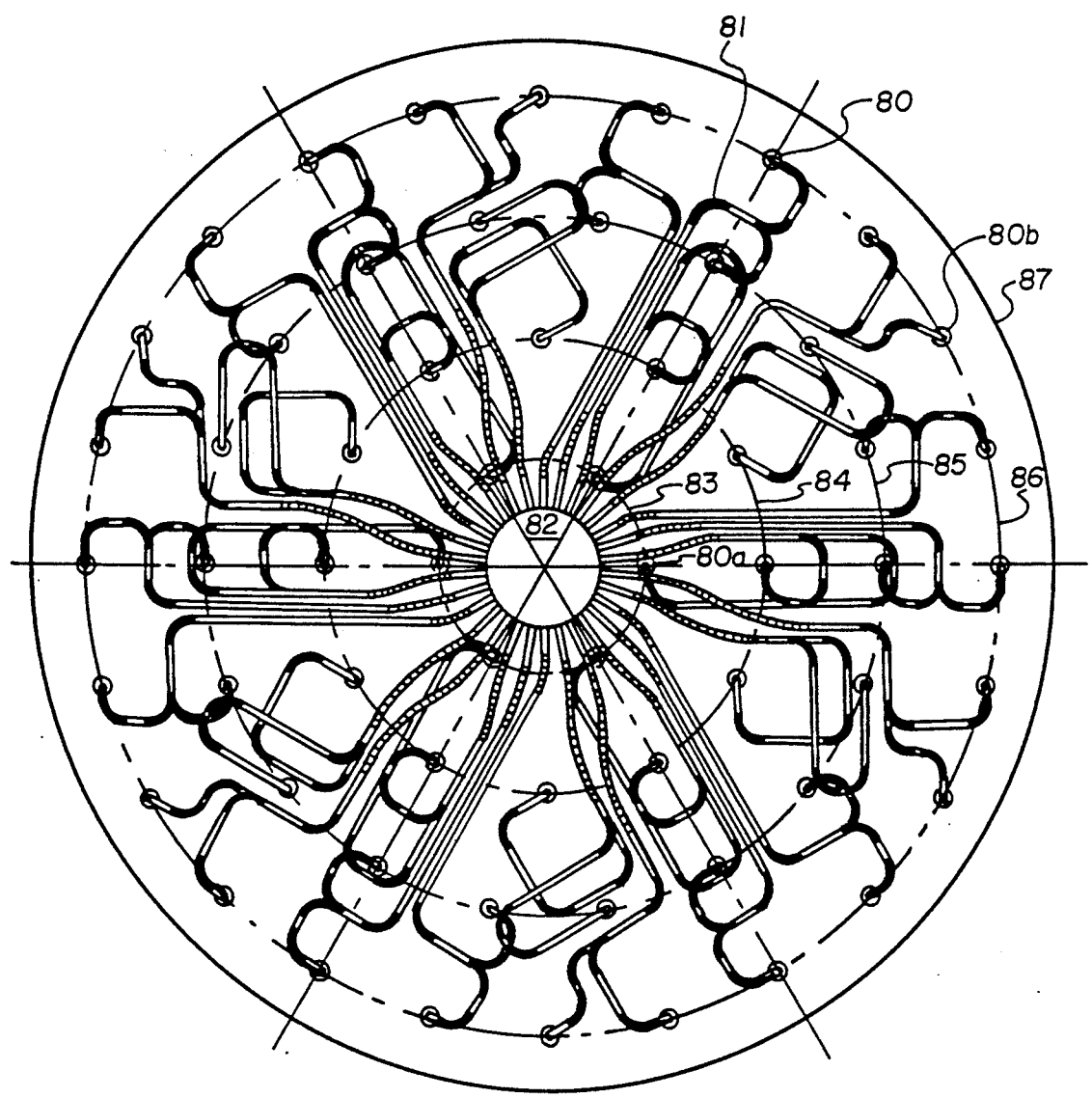
FIG. 5 is a plan view illustrating an alternative embodiment.

FIG. 5 illustrates the special circumstance in which all of the nozzles 80 are connected through tubing 81 to a common center well 82. The nozzles 80 are arranged in a pattern comprising concentric circles 83, 84, 85, 86. The radial distance between the circle 83 defined by the innermost nozzles 80a with center well 82 is approximately one-half the radial distance between adjacent intermediate circles 83, 84, 85, 86, respectively. The radial distance between the circle 86 defined by the outermost nozzles 80b and the wall 87 is similarly approximately one-half the radial distance between the intermediate circles. The nozzles 80 defining each of the circles 83, 84, 85, 86 are approximately equally spaced. As illustrated, the tubing runs 81 are of approximately equal length with hydraulically equivalent bends. (Each run 81 includes three approximately 90° elbow bends.) The tubing runs 81 extend from the center well 82 in two standard radial arrays. The pattern illustrated is particularly suitable for cells of smaller diameter; e.g., about 2 to about 8 feet. It is also useful in patterns having lower nozzle density. As nozzle density is increased, step-down plenums become more important as a means for reducing the density of the conduits in the manifold (header) system.

Figure 6:
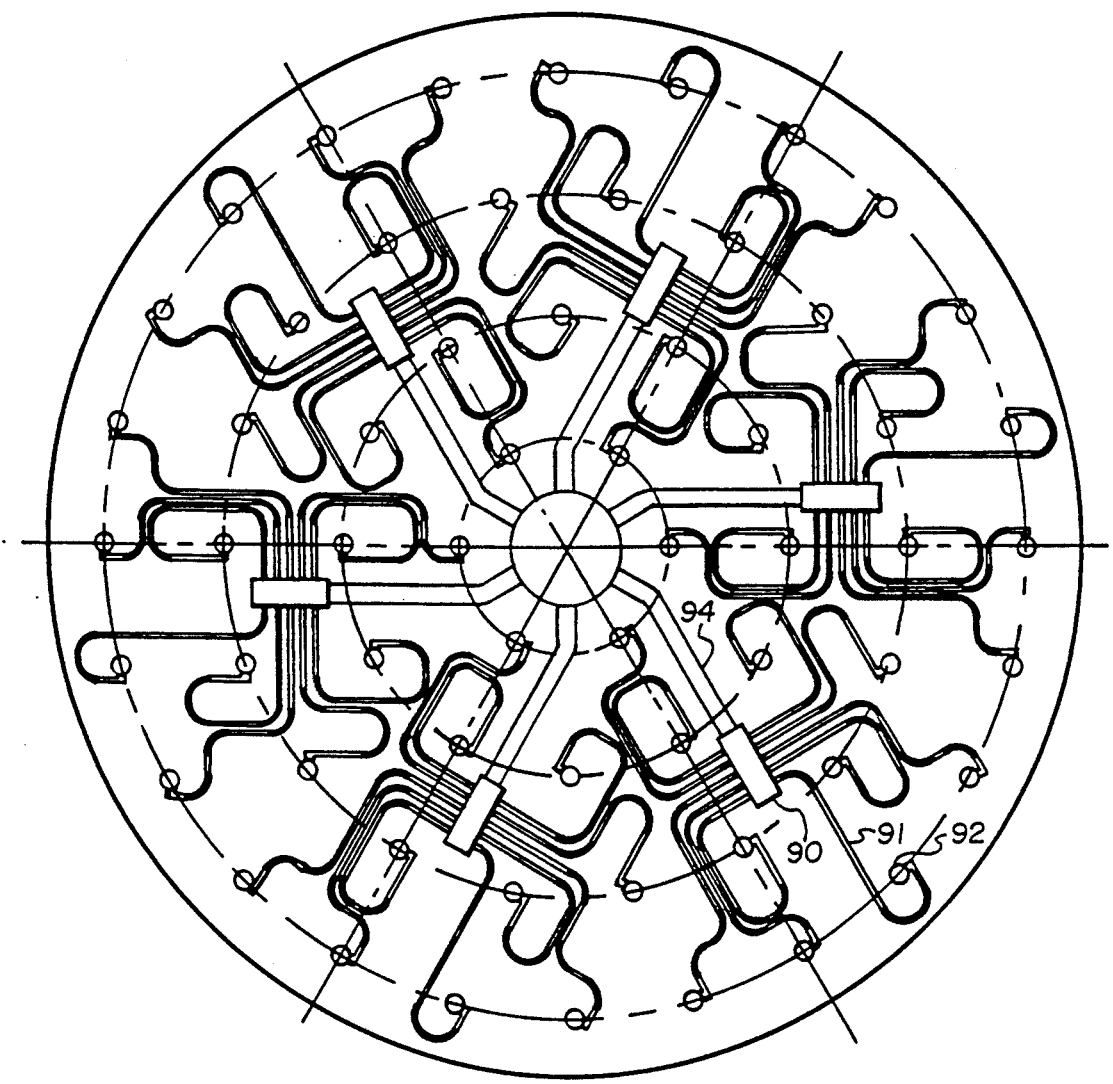
FIG. 6 is a plan view of another alternative embodiment.

FIG. 6 illustrates an alternative manifold arrangement which is specifically adapted to position an intermediate plenum 90 and tubing runs 91, nozzles 92 and primary conduits 94 for connecting to a structure (e.g. 55, FIGS. 1 and 2) out of substantial contact with resin; i.e., within a relatively narrow cross-sectional zone (e.g., 54, FIG. 2). The intermediate plenums 90 are not ideally symmetrical in this case, but appropriate hydraulic adjustments can be made to equalize the flow in the various tubing runs 91 associated with a particular plenum if desired. In many applications, no such adjustment is required.

Reference herein to the details of the illustrated embodiments is not intended to restrict the scope of the appended claims.

What is claimed:

1. An improved liquid transfer manifold system for maintaining an interface between liquid phases within a large scale separator system, including:
   a cell of a large scale separator system into which liquid is introduced as separated discrete phases at an inlet zone occupying a first approximately transverse cross-sectional region of said cell whereby to develop a discrete liquid phase plug which migrates approximately longitudinally in a direction normal said first cross-sectional region towards an outlet zone occupying a second approximately transverse cross-sectional region of said cell;
   said improved manifold system comprising:
   a center well, positioned approximately at the center of one of said transverse cross-sectional regions;
   a plurality of approximately hydraulically identical primary conduits, each including a proximal end in open liquid flow communication with said center well and a remote end;

a plurality of intermediate plenums, corresponding in number to said primary conduits, each said intermediate plenum being in open liquid flow communication with a respective said remote end of a respective said primary conduit;

a plurality, corresponding in number to said intermediate plenums, of sets of approximately hydraulically identical secondary conduits, each of said secondary conduits within each respective said set including a proximal end in open liquid flow communication with a respective said intermediate plenum; and a plurality of groups of liquid passage devices, each said group including a plurality of individual said devices, the total population of said devices being approximately evenly distributed at a plurality of distances from said center well throughout a cross-sectional region of said cell, each said device within each said group being connected through approximately hydraulically identical liquid distribution means to a respective said intermediate plenum;

wherein said manifold system provides a multiplicity of approximately hydraulically identical flow paths between said center well and said cell constructed and arranged for simultaneously providing a nearly identical flow rate in each said liquid passage device and maintaining an interface between liquid phases in passage through said manifold system.

2. A manifold system according to claim 1 wherein said approximately hydraulically identical liquid distribution means comprises:

a plurality, corresponding in number to said groups of liquid passage devices, of terminal plenums, each said terminal plenum being connected in open liquid flow communication to a said secondary conduit and to each of said devices within a respective said group of liquid passage devices.

3. A manifold system according to claim 2 wherein said liquid passage devices are selected from the group consisting essentially of liquid delivery devices and liquid receiving devices.

4. A manifold system according to claim 3 wherein all of said center well, primary conduits, intermediate plenums, secondary conduits, and liquid passage devices are mounted to structure defining a boundary of the cross-sectional zone occupied by said well.

5. A manifold system according to claim 4 wherein said structure comprises an end plate for said cell.

6. A liquid transfer manifold system according to claim 1, wherein:

a first manifold is mounted at an inlet end of said cell for introducing said liquid into said inlet zone, said cell having an approximately uniform transverse cross-section; said cell also having an outlet end; and a second manifold mounted at said outlet end comprising features identical to those of said first manifold for collecting said liquid from said outlet zone of said cell.

* * * * *